US009610187B2

(12) United States Patent
Bue, Jr.

(10) Patent No.: US 9,610,187 B2
(45) Date of Patent: Apr. 4, 2017

(54) TOPICAL PROPRIOCEPTIVE ACL TUBE AND METHODS OF USE

(75) Inventor: William D. Bue, Jr., Austin, TX (US)

(73) Assignee: Topical Gear, LLC, Lakeway, TX (US)

( * ) Notice: Subject to any disclaimer, the term of this patent is extended or adjusted under 35 U.S.C. 154(b) by 508 days.

(21) Appl. No.: 14/119,562

(22) PCT Filed: May 25, 2012

(86) PCT No.: PCT/US2012/039748
§ 371 (c)(1),
(2), (4) Date: Nov. 22, 2013

(87) PCT Pub. No.: WO2012/162682
PCT Pub. Date: Nov. 29, 2012

(65) Prior Publication Data
US 2014/0088478 A1    Mar. 27, 2014

Related U.S. Application Data

(60) Provisional application No. 61/490,020, filed on May 25, 2011.

(51) Int. Cl.
*A61F 5/01* (2006.01)
*A61H 1/00* (2006.01)
*A61F 5/30* (2006.01)

(52) U.S. Cl.
CPC .......... *A61F 5/0123* (2013.01); *A61F 5/0109* (2013.01); *A61F 5/30* (2013.01); *A61H 1/006* (2013.01)

(58) Field of Classification Search
CPC ........ A61F 5/0106; A61F 5/0109; A61F 5/30; A61F 5/0104; A61F 5/0123; A61H 1/006
USPC .................................................... 602/63, 62
See application file for complete search history.

(56) References Cited

U.S. PATENT DOCUMENTS

| 4,084,584 A | 4/1978 | Detty |
| 5,267,928 A | 12/1993 | Barile et al. |
| 5,810,753 A * | 9/1998 | Eberbach .............. A61F 5/0118 602/20 |

(Continued)

FOREIGN PATENT DOCUMENTS

| DE | 9417221 U1 | 1/1995 |
| EP | 0 262 638 A2 | 4/1988 |

OTHER PUBLICATIONS

International Search Report for PCT/US2012/039748 dated Sep. 21, 2012.

(Continued)

*Primary Examiner* — Kari Petrik
(74) *Attorney, Agent, or Firm* — Rodney J. Fuller; Booth Udall Fuller, PLC

(57) ABSTRACT

A topical proprioceptive tube and method of use for enhancing performance, reducing the risk of knee injury, or both. The tube includes a flexible sleeve having at least: a hamstring buttress, a knee buttress, or both, wherein the hamstring buttress and the knee buttress are configured to be coupled to the interior of the flexible sleeve such that the hamstring buttress applies pressure to at least a portion of one of the subject's hamstring muscles and the knee buttress applies pressure to at least a portion of the subject's Vastus Medialis Obliquus (VMO) when worn by the subject to provide the desired effect.

20 Claims, 6 Drawing Sheets

(56) References Cited

U.S. PATENT DOCUMENTS

| | | |
|---|---|---|
| 5,968,002 A | 10/1999 | Morrisseau |
| 6,135,974 A | 10/2000 | Matz |
| 2005/0154336 A1 | 7/2005 | Kloecker et al. |
| 2005/0261617 A1 | 11/2005 | Hall |
| 2007/0021699 A1 | 1/2007 | Braunstein et al. |
| 2008/0125842 A1 | 5/2008 | Petitt |

OTHER PUBLICATIONS

Written Opinion of the International Searching Authority for PCT/US2012/039748 dated Sep. 21, 2012.
International Preliminary Report on Patentability for PCT/US2012/039748 dated May 2, 2013.

\* cited by examiner

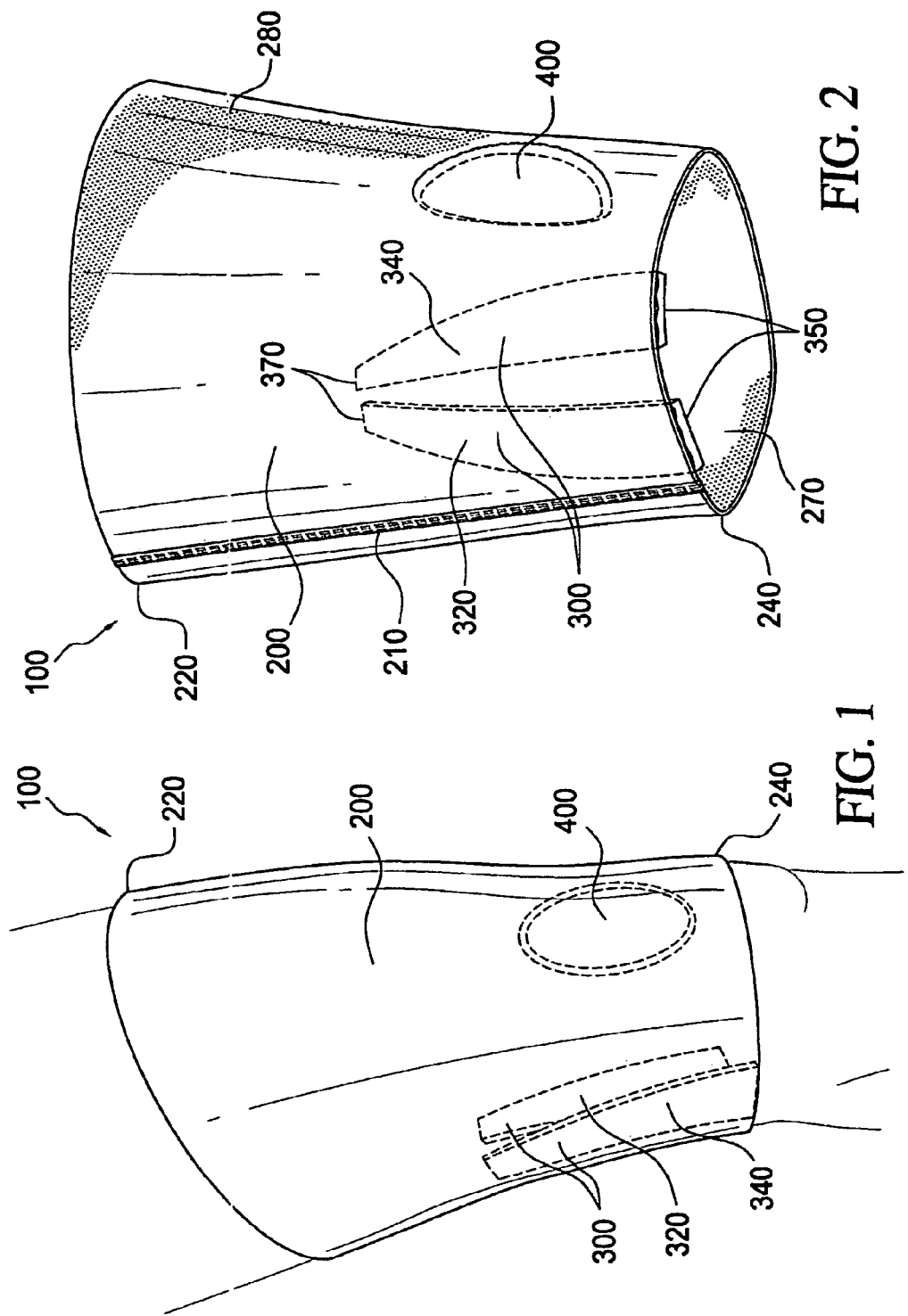

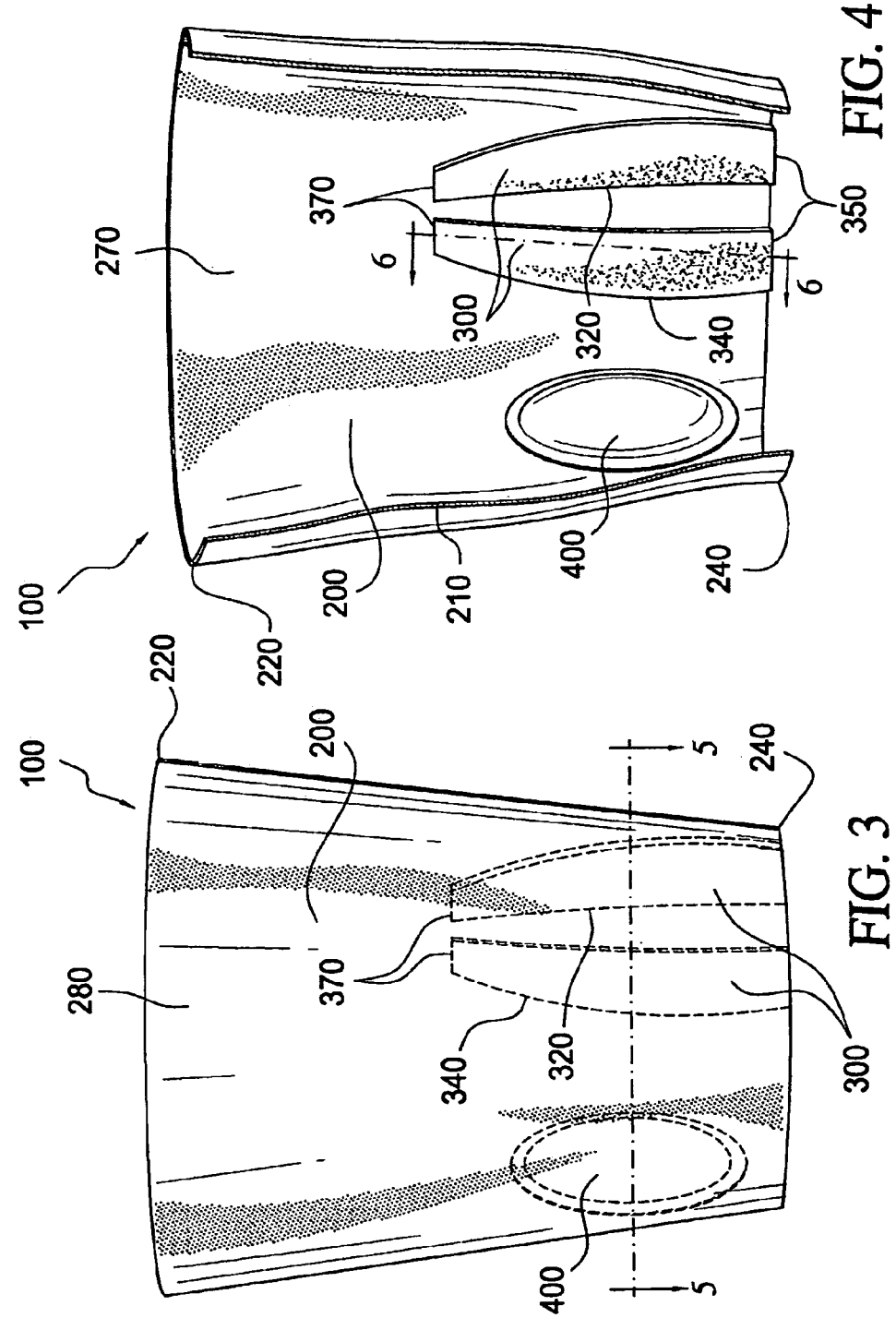

TOPICAL PROPRIOCEPTIVE ACL TUBE AND METHODS OF USE

RELATED APPLICATION DATA

This application is the U.S. National Stage of International Application No. PCT/US2012/039748, filed May 25, 2012, which claims the benefit of U.S. Provisional Application No. 61/490,020, filed May 25, 2011, the contents of each of which are herein expressly incorporated by reference for all purposes.

BACKGROUND OF THE INVENTION

1. Field of the Invention

The present invention relates generally to a medical device designed to enhance performance and reduce the risk of injury to the knee. Comprised of a flexible sleeve with strategically positioned hamstring and knee buttresses, the Anterior Cruciate Ligament Tube ("ACL Tube") of the present invention is designed to be worn during periods of physical activity or while at rest. In a preferred embodiment, each component of the ACL Tube is composed of resilient, non-rigid material, and the invention increases proprioception and reduces the risk of injury by applying pressure to the hamstring muscles and/or the Vastus Medialis Obliquus ("VMO") of a human subject.

2. Discussion of the Background

Injuries to the Anterior Cruciate Ligament ("ACL") are among the most feared by athletes of any sport. This year alone, it is estimated that over a quarter million people will tear their ACL. Roughly 70% of these injuries will require surgical reconstruction at a cost of $17,000 to $25,000 per injury. Indeed, injuries to the ACL are the most common knee ligament injuries. Although the affected individual is able to return to sports in 80-95% of cases, the long-term effects of an ACL tear negatively impact one's quality of life for many years thereafter.

One skilled in the art recognizes that the term "knee" refers to the complex synovial joint in humans that joins the thigh with the leg and consists of two articulations: one between the femur and tibia, and one between the femur and patella. The knee actually comprises three functional compartments: the femoropatellar, or "kneecap", the patellar groove; and the medial and lateral femorotibial articulations linking the femur, or thigh bone, with the tibia, the main bone of the lower leg.

The ACL is one of the four primary ligaments in the human knee (the others being the medial collateral ligament, the posterior cruciate ligament, and the lateral collateral ligament). As used herein, the term "knee injury" refers to a tear, rupture, or other injury to one or more of these ligaments, or to any dislocation, tracking, or other injury to the patella. The ACL extends between the "notch" of the distal femur and the medial wall of the lateral femoral condyle. The two fibrous bundles comprising the ACL are named for where they attach to the tibial plateau: the anteromedial and the posterolateral. The ACL attaches to the (anterior) intercondyloid eminence of the tibia, where it blends with the anterior horn of the lateral meniscus. These attachments provide stability to the knee joint by preventing anterior translation of the tibia in relation to the femur.

Interestingly, ACL tears occur disproportionately among women. Research indicates that women who participate in comparable jumping and cutting athletic activities tear their ACL two-to-nine times more often than their male counterparts. Experts have advanced a number of theories to explain this imbalance, including relative differences in environment, lower limb alignment, muscular strength, jump biomechanics, neuromuscular traits, hormone levels, and fitness level (conditioning). According to one theory, women experience higher rates of ACL tears because their hamstrings and quadriceps contract in a different order and at a different rate than do those of men. When men return to the ground after a vertical jump, their hamstrings generally contract before their quadriceps. This keeps the tibia posterior and protects the ACL from injury. When many women return to the ground after a vertical jump, however, the quadriceps fire first and the knee rotates internally. This physiological response places excessive strain on a woman's knees and may cause injury to her ACL. Thus, knee abduction loading appears to be a critical factor that contributes to the rupture of the ACL. Female athletes generate greater abduction loads when cutting and landing (compared to their male counterparts).

It is therefore hypothesized that knee abduction is a critical factor that contributes to the increased incidence of ACL injuries among women. See, e.g., Palmieri-Smith et. al, "Association of Quadriceps and Hamstrings Cocontraction Patterns with Knee Joint Loading", *Journal of Athletic Training*, 2009; 44(3):256-63.

The above study found that women experience lower overall quadriceps-to-hamstrings (Q:H) cocontraction, and that medial-to-lateral Q:H cocontraction appears to be particularly unbalanced in women. This imbalance limits the ability of female athletes to resist abduction loading. This may account for the added incidence of ACL injuries among women, because increased abduction loads create added strain on the ACL. In other words, the experimental and epidemiological evidence suggests that female athletes unwittingly utilize a selective Q:H activation strategy that contributes to abduction loading—a critical factor in the ACL rupture mechanism. Rather than evenly cocontracting the muscles that control abduction loading, women appear to contract the lateral quadriceps and hamstrings while underactivating the medial thigh muscles. Selective activation of the medial knee muscles helps to resist abduction loads. Thus, the pattern of Q:H contraction in women appears harmful to the ACL. In contrast, balanced cocontraction of the quadriceps and hamstrings (in the so-called frontal plane) enhances joint compression, which increases the stability of the knee joint. Overall, the existing research indicates that Q:H cocontraction is lower among female athletes as compared to their male counterparts.

Moreover, women typically have wider hips and a smaller femoral "notch" (to which the proximal end of the ACL attaches). These unique physiological and biomechanical characteristics observed among female athletes often cause greater internal rotation of the knee and result in an increased incidence of ACL injuries.

Unfortunately, contemporary athletic training programs and orthopedic devices fail to compensate for these unique female characteristics. Existing knee braces and athletic training methods utilize "one-size-fits-all" solutions that all too often focus on men to the exclusion of women. A need exists, therefore, for a device and training method designed to address the unique neurophysiological relationship between the quadriceps, hamstrings, and the ACL in women. Specifically, a need exists for a proprioceptive knee device configured to lower the risk of knee injuries, especially in women athletes. Such a device would preferably enhance neuromuscular communication to coordinate hamstring and quadriceps contraction in women to lower the risk of knee injuries.

SUMMARY OF THE INVENTION

The objective of the present invention is to provide a therapeutic proprioceptive device and method of use for enhancing performance and reducing the risk of knee injury. Instead of a bulky, ill-fitting knee brace commonly used in the art, the present invention employs a topical proprioceptive ACL tube with a flexible sleeve comprising an upper end and a lower end, the upper end and the lower end each having an interior and an exterior surface; and one or more hamstring buttresses having a base portion and a upper portion, the one or more hamstring buttresses being coupled to the interior of the flexible sleeve so that the one or more hamstring buttresses are over at least one of the subject's hamstring muscles, the base portion being coupled towards the lower end of the flexible sleeve and the upper portion being coupled towards the upper end of the flexible sleeve, wherein the one or more hamstring buttresses are configured to apply sufficient pressure to at least one of the subject's hamstring muscles when worn; and one or more knee buttresses coupled to the interior surface of the flexible sleeve so that the one or more knee buttresses is over the subject's Vastus Medialis Obliquus (VMO), the one or more knee buttresses comprising: a pad comprised of resilient material, the pad being configured to apply pressure to the VMO when worn by the subject.

The ACL tube of the present invention is uniquely designed to stimulate Q:H cocontraction and reduce incidences of patellar tracking. The present invention further comprises methods of use, wherein the topical ACL tube is applied to the subject's knee during physical activities.

The present invention is also directed to a therapeutic proprioceptive method for enhancing performance and reducing the risk of knee injury in a human subject by enhancing cocontraction of the subject's quadriceps and hamstrings, said method comprising the steps of:

(a) stimulating neuromuscular communication with the hamstrings by applying topical pressure to at least one of the subject's hamstring muscles;

(b) stimulating neuromuscular communication with the knee and reducing patellar tracking by applying topical pressure to the VMO; and (c) reducing the abduction load on the knee by the concurrent topical application of (a) and (b).

BRIEF DESCRIPTION OF THE DRAWINGS

The accompanying drawings, described below, illustrate preferred embodiments of the present invention. It will be understood that no limitation to the scope of the invention is intended thereby. These drawings depict various features and further advantages of the present invention. The invention is not limited to the particular embodiments disclosed in these drawings, as it should be understood by one skilled in the art that additional features, modifications, and alternative embodiments are contemplated by the invention as disclosed herein.

FIG. 1 is a front and side perspective view of a preferred embodiment of the present invention showing the device on a subject's leg.

FIG. 2 is a front perspective view of a preferred embodiment of the present invention.

FIG. 3 is a front elevational view of a preferred embodiment of the present invention showing the device in the Open position.

FIG. 4 is an alternate rear elevational view of a preferred embodiment of the present invention.

DETAILED DESCRIPTION OF THE PREFERRED EMBODIMENTS

The following is a description of the preferred embodiments of the present invention and is not intended to limit the scope of the invention to the particular embodiments discussed below.

Figure 6:
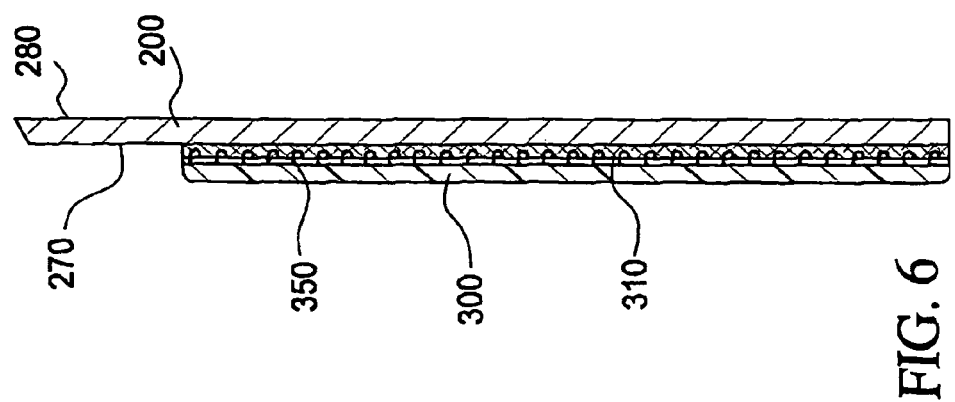
FIG. 6 is a front elevational view of a preferred embodiment of the present invention showing a hamstring buttress optionally attached via hook and loop fasteners.
Figure 5:
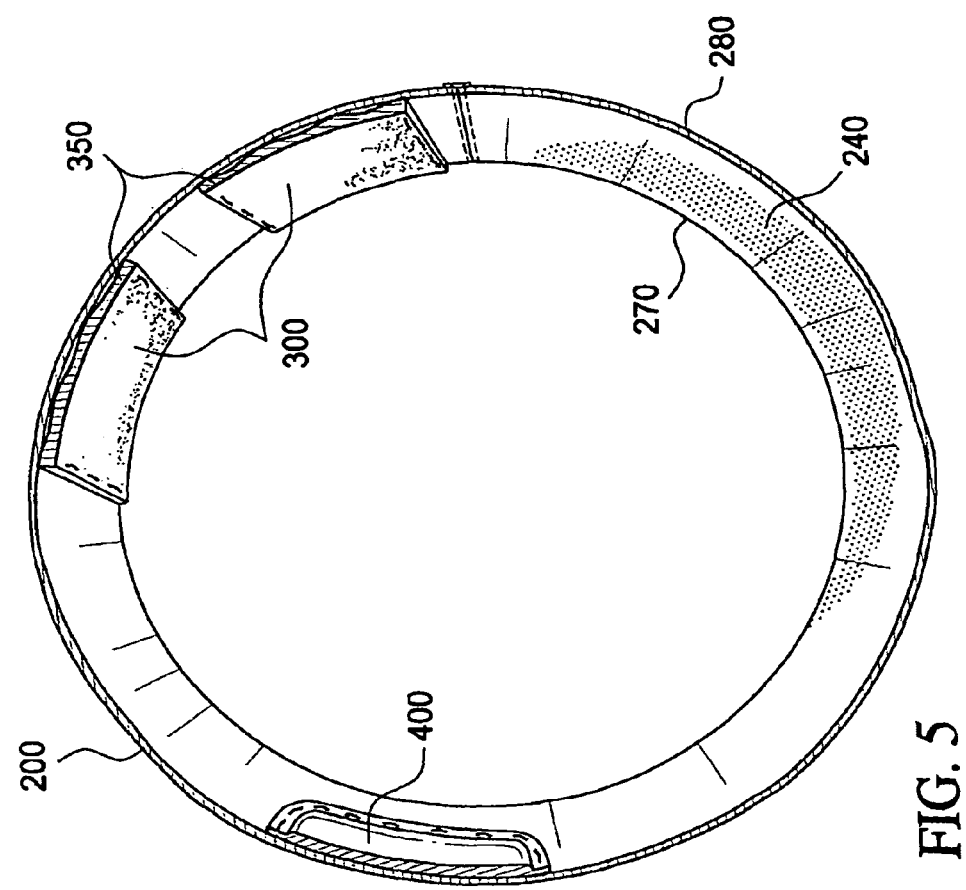
FIG. 5 is a bottom plan view of a preferred embodiment of the present invention.
Figure 8:
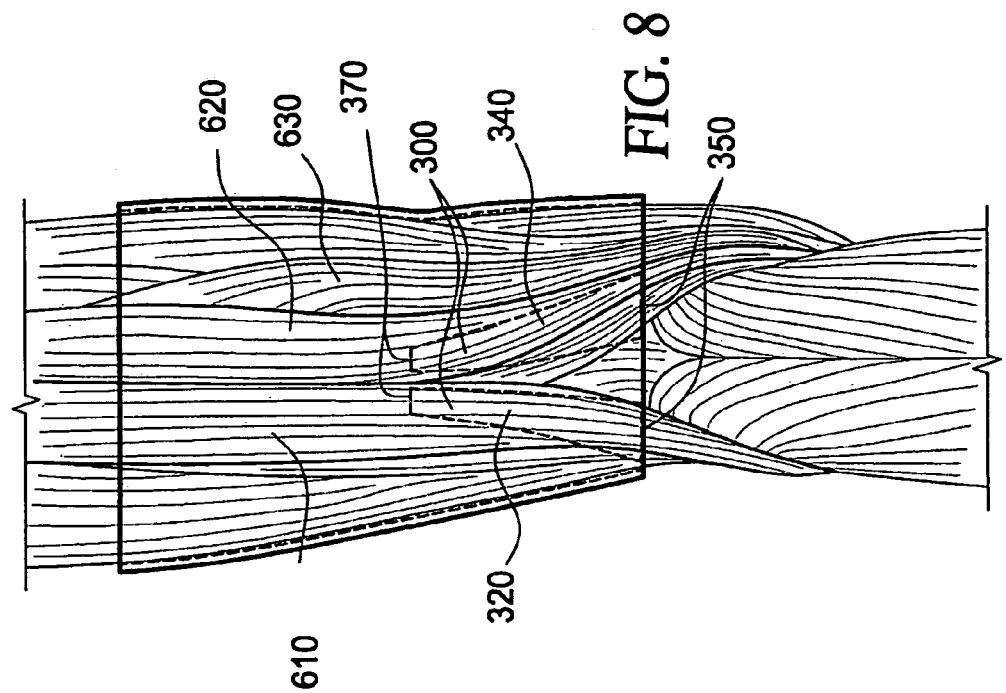
FIG. 8 is a rear elevational view of a preferred embodiment of the present invention showing the device on the leg of a human subject.
Figure 7:
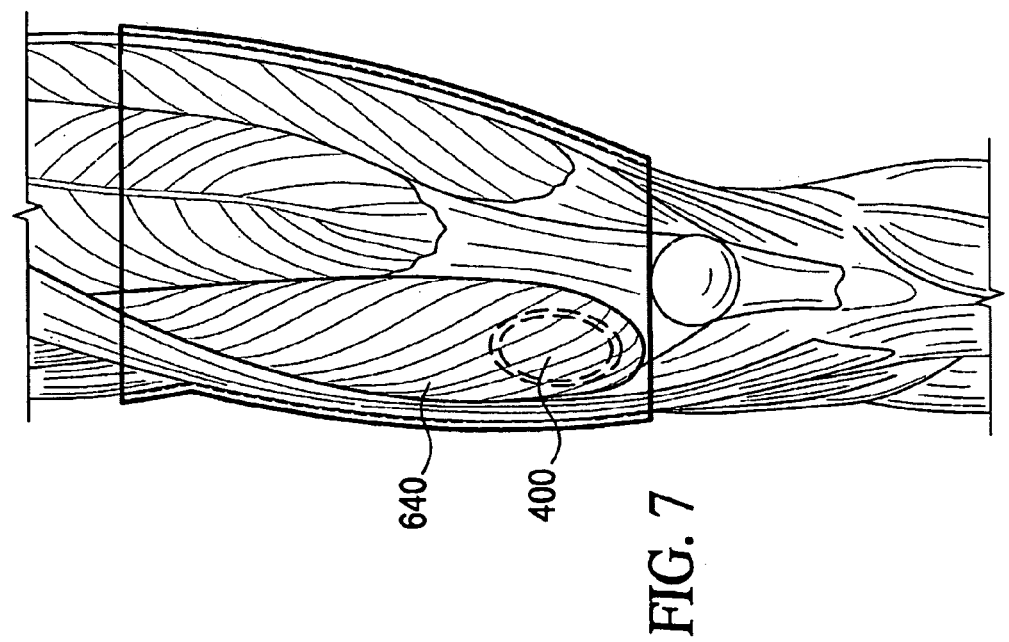
FIG. 7 is a front elevational view of a preferred embodiment of the present invention showing the device on the leg of a human subject.
Figure 10:
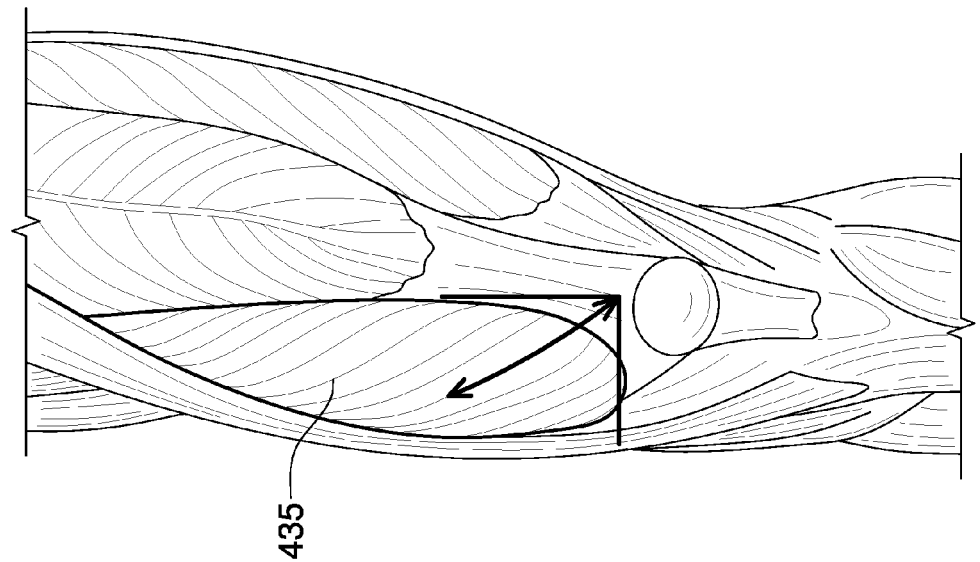
FIG. 10 is a front elevational view of a preferred embodiment of the present invention showing the device on the leg of a human subject.
Figure 9:
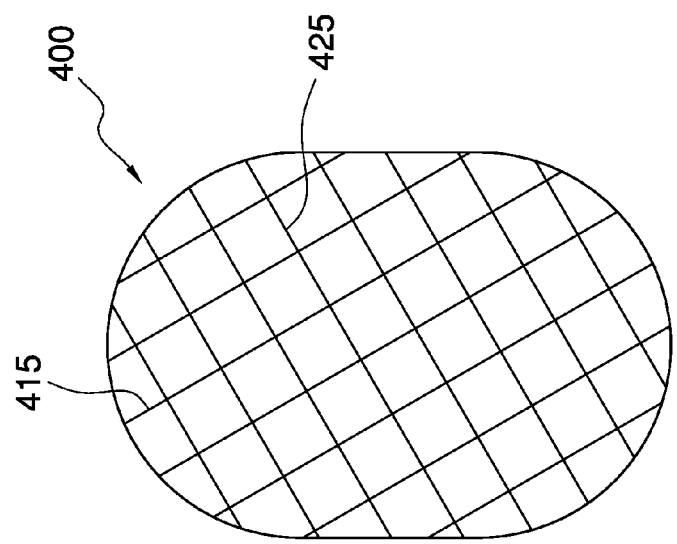
FIG. 9 is a bottom plain view of a preferred embodiment of the present invention showing a grid of rounded lines on an outer surface of a knee buttress.
Figure 12:
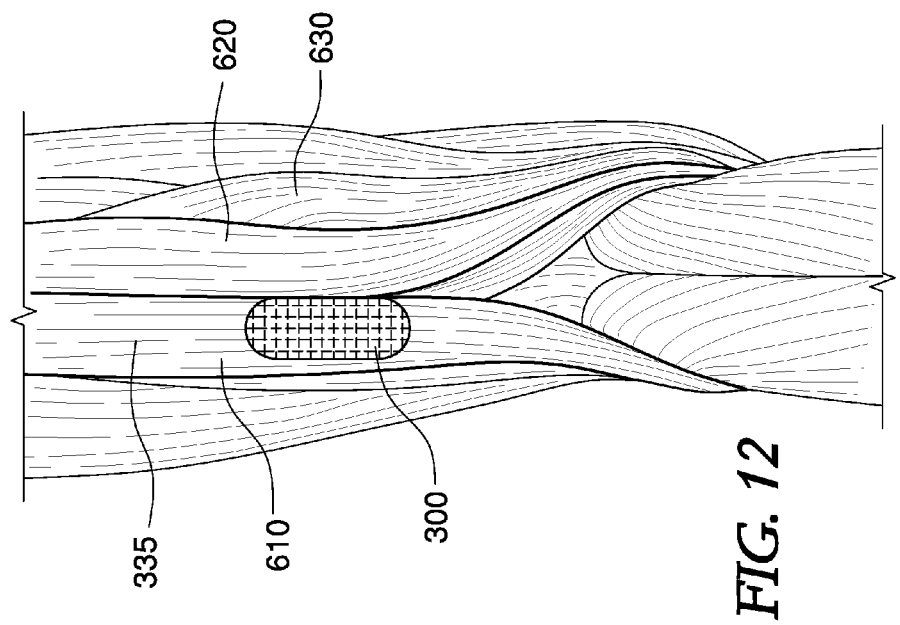
FIG. 12 is a front elevational view of a preferred embodiment of the present invention showing the device on the leg of a human subject.
Figure 11:
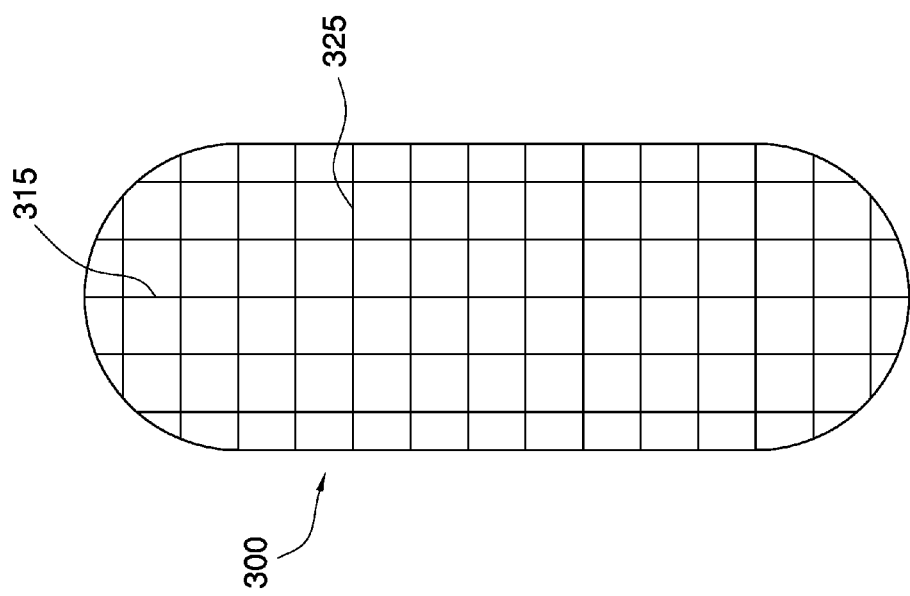
FIG. 11 is a bottom plain view of a preferred embodiment of the present invention showing a grid of rounded lines on an outer surface of a hamstring buttress.

In accordance with the present invention, FIGS. 1-8 depict topical proprioceptive ACL Tube 100 for enhancing performance and reducing the risk of knee injuries in human subjects, including women athletes. In a preferred embodiment, topical ACL tube 100 includes flexible sleeve 200, which is comprised of a lower end 240 and an upper end 220, the upper end 220 and the lower end 240 each having an interior surface 270 and an exterior surface 280. Flexible sleeve 200 is preferably comprised of a thin, resilient, radially stretchable material designed to conform and contour to a subject's knee. Preferably, flexible sleeve 200 is comprised of a loose-knit fiber breathably configured to release perspiration and allow air flow during use. The loose-knit fiber can be any one of a number of commercially available stretchable materials such as LYCRA, SPANDEX, BIOSKIN, or EpX. More preferably, the material is a tri-laminate (bonded) material having a first polyurethance-polyurea copolymer on the inside and a second polyurethane-polyurea copolymer on the outside, with a thin polyurethane membrane between the first and second copolymers. In a preferred embodiment, the tri-laminate material is less than 2 mm thick and is sufficiently elastic to provide between 15-25 mm Hg compression to the lower leg, ankle, and/or foot of the subject. As shown in FIGS. 3-4, flexible sleeve 200 is stitched together and vertically bisected along seam 210. Optionally, seam 210 is comprised of one or more hook-loop fasteners suitable for releasably coupling the proximal and distal ends of flexible sleeve 200 together along seam 210.

Preferably, the lower (distal) end 240 of flexible sleeve 200 terminates at the superior (top) portion of the patella and the upper (proximal) end 220 terminates approximately between 2.54 cm and 12.7 cm below the gluteal fold. Preferably, upper end 220 of flexible sleeve 200 terminates at least 7.62 cm below the gluteal fold.

In an alternate embodiment, lower end 240 of flexible sleeve 200 extends beyond the patella and terminates in the upper calf region of the lower leg of a subject. Advantageously, this alternative embodiment may include one or more apertures 290 encircling the patella.

Advantageously, topical ACL tube 100 further comprises one or more hamstring buttresses 300. Preferably, topical ACL tube 100 includes a medial hamstring buttress 320 and a biceps femoris buttress 340, wherein both the medial hamstring buttress 320 and the biceps femoris buttress 340 are coupled to the interior surface 270 of the lower end 240 of flexible sleeve 200 and extend into the interior surface 270 of the upper end 220 of flexible sleeve 200. More preferably, the two hamstring buttresses 300 are mirror images of each other and comprise a lower (distal) base portion 350 and an upper (proximal) portion 370. Most preferably, the two hamstring buttresses 300 are positioned in the sleeve such that when the topical ACL tube 100 is worn by the subject, both medial hamstring buttress 320 and biceps femoris buttress 340 extend over and apply pressure to the medial hamstring muscles (the semimembranosus and the semitendinosus) and the biceps femoris, respectively. Preferably, medial hamstring buttress 320 is centered over the medial hamstring muscles at approximately 50% of thigh length (measured between the front tip of the hip at the anterior superior iliac spine and the knee joint line). Preferably, the hamstring buttresses 300 are positioned such that the upper (proximal) portion 370 is approximately between 2.54 cm and 12.7 cm below the gluteal fold. More preferably, the upper portion 370 of hamstring buttresses 300 is between 5.08 cm and 10.16 cm below the gluteal fold. Most preferably, hamstring buttresses 300 are positioned such that the upper (proximal) portion is between 7.62-8.89 inches below the gluteal fold.

In their preferred embodiments, hamstring buttresses 300 are oval or elliptical shaped. Preferably, each hamstring buttress 300 is between 2.54 cm and 12.7 cm long. More preferably, hamstring buttresses 300 are between 7.62 cm and 10.16 cm long. Most preferably, hamstring buttresses are 8.89 cm long. Advantageously, each hamstring buttress 300 is between 2 cm and 10.16 cm wide. More advantageously, each medial hamstring buttress 300 is between 5.08 cm and 7.62 cm wide. Most advantageously, medial hamstring buttresses 300 are 6.35 cm wide. Thus, in their preferred embodiments, hamstring buttresses 300 have a surface area of between 0.82 cm$^2$ and 135.48 cm$^2$. More preferably, hamstring buttresses 300 have a surface area of between 9.75 cm$^2$ and 77.42 cm$^2$.

Preferably, the amount of pressure applied to the hamstring muscles by hamstring buttresses 300 is between 15-400 mm Hg of compression. More preferably, the amount of pressure applied to the hamstring muscles by hamstring buttresses 300 is between 25-350 mm HG compression. Most preferably, the amount of pressure applied to the hamstring muscles by hamstring buttresses 300 is between 35-200 mm HG compression. In a preferred embodiment, hamstring buttress 320 applies more pressure to the medial hamstring muscles than biceps femoris buttress 340 applies to the biceps femoris. In an alternate embodiment, hamstring buttress 320 applies less pressure to the medial hamstring muscles than biceps femoris buttress 340 does to the biceps femoris. In another alternative embodiment, medial hamstring buttress 320 applies the same amount of pressure to the medial hamstring as the biceps femoris buttress 340 applies to the biceps femoris.

In a preferred embodiment, hamstring buttresses 300 are comprised of a compressible material. Preferably, the compressible material is comprised of one or more of the following: foam or foam-like material, a gel or gel-like material, or any other compressible material suitable to apply pressure to the hamstring muscles and receptors. Preferably, flexible sleeve 200 compresses hamstring buttresses 300 toward the subject's hamstrings with a force sufficient to stimulate sensory and tactile receptors located in the hamstring region. Most preferably, the hamstring buttresses 300 extend over and apply pressure to the semitendinosus, semimembranosus, biceps femoris, and/or popliteal fossa. Preferably, hamstring buttresses 300 further comprise two sets of grid lines 315, 325 on the outer surface of the medial hamstring buttress 320 and the biceps femoris buttress 340. Preferably, the first set of grid lines 315 run parallel to the medial hamstring muscle fibers 335 and the second set of grid lines 325 run perpendicular to the medial hamstring muscle fibers. Preferably, each rounded grid line 315, 325 is between 0.16 cm and 1.27 cm wide and between 0.32 cm and 2.54 cm deep. More preferably, each rounded grid line 315, 325 is between 0.32 cm and 0.64 cm wide and between 0.64 cm and 1.28 cm deep (perpendicular lines may be deeper in order to enhance proprioception). The preferred rounded grid lines 315, 325 are typically grooves formed below the horizon of the hamstring buttress's outer surface. Alternatively, however, the grid lines 315, 325 can also rise above the surface of the hamstring buttresses and provide the required effect.

Preferably, hamstring buttresses 300 are releasably coupled to the interior of flexible sleeve 200. More preferably, hamstring buttresses 300 are further comprised of hook loop fasteners 350 affixed to the interior portion 310 of the hamstring buttresses 300, wherein the hook loop fasteners are suitable for releasably coupling the interior portion 310 of hamstring buttresses 300 to the interior surface 270 of flexible sleeve 200. Most preferably, both hamstring buttress 320 and biceps femoris buttress 340 are releasably coupled to the interior surface 270 of the lower end 240 of flexible sleeve 200.

Advantageously, topical ACL tube 100 further comprises one or more knee buttresses 400 coupled to the interior surface 270 of the lower end 240 of flexible sleeve 200. Preferably, the one or more knee buttresses 400 comprise an oval or elliptical shaped pad comprised of resilient material, wherein the pad is configured to extend at least partially over and apply pressure to the subject's Vastus Medialis Obliquus (VMO). Preferably, knee buttress 400 is centered over the medial hamstring muscles at approximately 67% of thigh length (measured between the front tip of the hip at the anterior superior iliac spine and the knee joint line). Advantageously, knee buttress 400 is between 2.54 cm and 7.62 cm wide and 5.08 cm and 10.16 cm long. More advantageously, knee buttress 400 is 5.08 cm wide and 7.62 cm long. In a preferred embodiment, the surface area of the knee buttress 400 is between 0.1-135.48 cm. More preferably, the surface area of knee buttress 400 is between 7.62 cm$^2$ and 67.74 cm$^2$. In a preferred embodiment, the distal end of buttress 400 terminates 1.27 cm to 5.08 cm above the patella. More preferably, the distal end of buttress 400 terminates 2.54 cm to 3.81 cm above the patella.

Preferably, the amount of pressure applied to the VMO is between 15-400 mm Hg of compression. More preferably, the amount of pressure applied to the VMO by knee buttress 400 is between 25-350 mm HG compression. Most preferably, the amount of pressure applied to the VMO by knee buttress 400 is between 35-200 mm HG compression.

Preferably, knee buttresses 400 further comprise two sets of grid lines 415 on the outer surface 405 of the knee buttress 400. Preferably, the first set of grid lines 415 run parallel to the Vastus Medialis Obliquus (VMO) muscle fibers 435 and the second set of grid lines 425 run perpendicular to the Vastus Medialis Obliquus (VMO) muscle fibers 435. The first set of grid lines preferably run parallel to the Vastus Medialis Obliquus (VMO) muscle fibers 435 and are positioned at a 60 degree angle on the outer surface of the knee buttress 440 to provide the desired effect. Furthermore, each grid line 415, 425, preferably rounded, is between 0.32 cm and 0.64 cm wide and between 0.64 and 1.27 cm deep (perpendicular lines may be deeper in order to enhance proprioception). The preferred rounded grid lines are typically grooves formed below the horizon of the knee buttress's outer surface. Alternatively, however, the grid lines 415, 425 can also rise above the surface of the knee buttress and provide the required effect.

In a preferred embodiment, ACL Tube 100 comprises medial hamstring buttress 320, biceps femoris buttress 340, and knee buttress 400. Preferably, ACL Tube 100 is positioned on the leg and/or knee of the subject such that that medial hamstring buttress 320 and the biceps femoris buttress 340 extend substantially over and apply pressure to the hamstring muscles (the semimembranosus, semitendinosus, biceps femoris, and/or popliteal fossa) and knee buttress 400 extends substantially over and applies pressure to the VMO. More preferably, the ACL tube 100 is positioned such that: buttress 320 extends substantially over and applies pressure to the medial hamstring muscles, biceps femoris buttress 340 extends substantially over and applies pressure to the biceps femoris, and knee buttress 400 extends substantially over and applies pressure to the VMO. Advantageously, hamstring buttress 320 mirrors the medial hamstring musculature, biceps femoris buttress 340 mirrors the biceps femoris musculature, and knee buttress 400 mirrors the shape of the VMO. In alternate embodiments, hamstring buttress 320 and biceps femoris buttress 340 include a tapered base portion 350 and a wide upper portion 370. Alternatively, medial hamstring buttress 320 and biceps femoris buttress 340 include a wide base portion 350 and a tapered upper portion 370.

In an alternate embodiment, hamstring buttress 320 substantially covers (e.g., at least 50%, 60%, 70%, 80% or 90%) and applies pressure to the medial hamstring muscles but preferably does not substantially extend over or apply pressure to any other part of the leg or knee covered by flexible sleeve 200. In this embodiment, biceps femoris buttress 340 substantially covers and applies pressure to the semimembranosus and semitendinosus but preferably does not substantially extend over other part of the leg or knee covered by flexible sleeve 200. In this same embodiment, knee buttress 400 substantially covers and applies pressure to the VMO but does not extend over or apply pressure to any other part of the leg or knee covered by flexible sleeve 200.

Most preferably, hamstring buttress 320 is positioned such that it substantially covers and applies pressure to the medial hamstring musculature without radially extending into or intruding upon any other hamstring muscles or any ancillary portion of flexible sleeve 200. In this most preferred embodiment, biceps femoris buttress 340 substantially covers and applies pressure to the biceps femoris without radially extending into or intruding upon the medial hamstring muscles or any ancillary portion of flexible sleeve 200. In this same (most preferred) embodiment, knee buttress 400 substantially covers and applies pressure to the VMO but does not radially extend into or intrude upon the medial or lateral hamstring muscles or any ancillary portion of flexible sleeve 200. In its most preferred form, ACL tube 100 and flexible sleeve 200 are positioned such that biceps femoris buttress 340, hamstring buttress 320, and knee buttress 400 are each positioned as described hereinabove.

In one alternate embodiment, ACL tube 100 comprises only two buttresses affixed and/or releasably coupled to flexible sleeve 200: the medial hamstring buttress 320 and the knee buttress 400.

In an alternate embodiment, the ACL tube 100 of the present invention is included in a topical proprioceptive ACL tube kit. The kit includes, separately, flexible sleeve 200, one or more hamstring buttresses 300, and one or more knee buttresses 400. Preferably, the kit includes printed instructions 500 relating to the use of the topical ACL tube 100, including instructions to couple the hamstring buttresses 300 to the interior surface 270 of lower end 240 of flexible sleeve 200 such that hamstring buttresses 300 extend into the interior surface 270 of the upper end 220. More preferably, printed instructions 500 explain that hamstring buttresses 300 should be situated such that they extend over and apply pressure to the hamstring muscles as set forth above. Most preferably, printed instructions 500 explain that hamstring buttresses 300 should be situated such that they extend over and apply pressure to the semitendinosus 630, semimembranosus 620, biceps femorus 610, and/or popliteal fossa of the subject. Advantageously, printed instructions 500 further include instructions for coupling the one or more knee buttresses 400 to the interior surface 270 of the lower end 240 of flexible sleeve 200. Preferably, printed instructions 500 include specific instructions relating to the positioning of knee buttress 400 such that it extends at least partially over and applies pressure to the subject's Vastus Medialis Obliquus (VMO) 640.

The present invention also comprises methods of using the topical proprioceptive ACL tube 100 of the present invention for enhancing an athlete's performance and/or reducing the risk of a knee and/or hamstring injury. Method 600 comprises (1) applying the topical ACL tube of the present invention to the subject's knee (2) during physical activities (3) over an interval of time. Preferably, the injury prevented is an injury to the Anterior Cruciate Ligament (ACL).

In another alternative embodiment or embodiments, the above device is optionally configured to supply transcutaneous nerve stimulation (TENS), heat, and/or cold to subject-selected regions of upper end 220 and/or lower end 240.

Upon reading the teachings of this specification, those with ordinary skill in the art will appreciate that, under certain circumstances, considering issues such as changes in technology, subject requirements, etc., a variety of fastening devices may be used to "fasten," "secure", "releasably secure", and/or "releasably couple" one or more components of the present invention. These fasteners or fastening means may include one or more of the following: adhesives, bolts, buckles, clasps, latches, locks, screws, snaps, clamps, connectors, couplings, ties or other fastening means yet to be developed.

Likewise, upon reading the teachings of this specification, those with ordinary skill in the art will appreciate that, under certain circumstances, considering issues such as changes in technology, subject requirements, etc., a variety of fastening devices, such as adhesives, belts, bolts, buckles, clasps, latches, locks, screws, snaps, clamps, connectors, couplings, ties or other fastening means yet to be developed may be used in lieu of—or in conjunction with—any of the fasteners or fastening means discussed above.

Although applicant has described applicant's preferred embodiments of this invention, it will be understood that the broadest scope of this invention includes modifications. Such scope is limited only by the claims as read in connection with the above specification. Further, many other advantages of applicant's invention will be apparent to those skilled in the art from the above descriptions and the claims below.

I claim:

1. A topical proprioceptive tube for a human subject, comprising:
   a flexible sleeve comprising an interior surface configured to receive a buttress, wherein the topical proprioceptive tube comprises no more than two buttresses;
   a first buttress comprising a hamstring buttress, the hamstring buttress being adjustably coupled to the interior surface of the flexible sleeve and configured so that a size, orientation, and position of the hamstring buttress extends over at least a portion of the subject's semimembranosus and semitendinosus muscles when worn by the subject without extending over other parts of the leg or knee covered by the flexible sleeve; and
   a second buttress comprising a knee buttress adjustably coupled to the interior surface of the flexible sleeve and configured so that a size, orientation, and position of the knee buttress are disposed over at least a portion of the subject's Vastus Medialis Obliquus (VMO) when worn by the subject without extending over any other part of the leg or knee covered by the flexible sleeve.

2. The topical proprioceptive tube according to claim 1, wherein the hamstring buttress is between 2.54 cm and 12.7 cm long and between 2 cm and 10.16 cm wide.

3. The topical proprioceptive tube according to claim 1, wherein the amount of pressure the hamstring buttress and the knee buttress are configured to apply to the hamstring muscles is between 15-400 mm Hg.

4. The topical proprioceptive tube according to claim 1, wherein the knee buttresses is between 2.54 cm and 7.62 cm wide and between 5.08 cm and 10.16 cm long.

5. The topical proprioceptive tube according to claim 1, wherein the surface area of the knee buttress is between 7.62 cm$^2$ and 67.74 cm$^2$.

6. The topical proprioceptive tube according to claim 1, wherein the distal end of the knee buttress is configured to terminate 2.54 cm to 3.81 cm above the subject's patella.

7. A topical proprioceptive tube for a human subject, comprising:
   a flexible sleeve comprising an interior surface configured to receive a buttress, wherein the topical proprioceptive tube comprises no more than three buttresses;
   one or more hamstring buttresses being adjustably coupled to the interior surface of the flexible sleeve and configured so that a size, orientation, and position of the one or more hamstring buttresses extend over at least a portion of one of the subject's hamstring muscles when worn by the subject; and
   a knee buttress adjustably coupled to the interior surface of the flexible sleeve and configured so that a size, orientation, and position of the knee buttress are disposed over at least a portion of the subject's Vastus Medialis Obliquus (VMO) when worn by the subject without extending over any other part of the leg or knee covered by the flexible sleeve.

8. The topical proprioceptive tube according to claim 7, wherein at least one of the one or more hamstring buttresses is selected from the group consisting of:
   a first hamstring buttress configured to cover and apply pressure to the subject's medial hamstring muscles when worn by the subject without extending over any other part of the leg or knee covered by the flexible sleeve; and
   a second hamstring buttress configured to cover and apply pressure to the subject's semimembranosus and semitendinosus muscles when worn by the subject without extending over other parts of the leg or knee covered by the flexible sleeve.

9. The topical proprioceptive tube according to claim 7, wherein the one or more hamstring buttresses is configured to extend over and apply pressure to the semitendinosus, semimembranosus, biceps femoris, and/or popliteal fossa.

10. The topical proprioceptive tube according to claim 7, wherein each of the one or more hamstring buttresses is between 2.54 cm and 12.7 cm long and between 2.0 cm and 10.16 cm wide.

11. The topical proprioceptive tube according to claim 7, wherein the amount of pressure the one or more hamstring buttresses is configured to apply to the hamstring muscles is between 15-400 mm Hg.

12. The topical proprioceptive tube according to claim 7, wherein the one or more hamstring buttresses are comprised of a compressible material, suitable to apply pressure to the hamstring muscles and receptors.

13. A topical proprioceptive tube for a human subject, comprising:
   a flexible sleeve comprising an interior surface configured to receive a buttress;
   one or more hamstring buttresses configured to be adjustably coupled to the interior surface of the flexible sleeve and configured so that an orientation and position of the one or more hamstring buttresses extend over at least a portion of one of the subject's hamstring muscles when worn by the subject; and
   a knee buttress adjustably coupled to the interior surface of the flexible sleeve and configured so that a size, orientation, and position of the knee buttress are disposed over at least a portion of the subject's Vastus Medialis Obliquus (VMO) when worn by the subject without extending over any other part of the leg or knee covered by the flexible sleeve.

14. The topical proprioceptive tube according to claim 13, wherein the amount of pressure the one or more hamstring buttresses is configured to apply to the hamstring muscles is between 35-200 mm Hg.

15. The topical proprioceptive tube according to claim 13, wherein the one or more hamstring buttresses are comprised of a compressible material, suitable to apply pressure to the hamstring muscles and receptors.

16. The topical proprioceptive tube of claim 13, wherein the flexible sleeve is comprised of a tri-laminate bonded material comprising loose-knit fiber breathably configured to release perspiration and allow air-flow during use.

17. The topical proprioceptive tube according to claim 13, wherein the one or more hamstring buttresses comprises at least:
   a first hamstring buttress comprising a medial hamstring buttress configured to cover and apply pressure to the subject's medial hamstring muscles when worn by the subject without extending over any other part of the subject's leg or knee covered by the flexible sleeve; and
   a second hamstring buttress comprising a biceps femoris hamstring buttress configured to cover and apply pressure to the subject's biceps femoris muscle when worn by the subject without extending over other parts of the subject's leg or knee covered by the flexible sleeve.

18. The topical proprioceptive tube of claim 17, wherein the medial hamstring buttress is configured to apply less pressure to the medial hamstring muscles than the biceps femoris hamstring buttress applies to the biceps femoris muscle.

19. The topical proprioceptive tube of claim 17, wherein the medial hamstring buttress is configured to apply the same amount of pressure to the medial hamstring muscles as the biceps femoris hamstring buttress applies to the biceps femoris muscle.

20. The topical proprioceptive tube according to claim 13, wherein at least one of the one or more hamstring buttresses is selected from the group consisting of:
- a first hamstring buttress configured to cover and apply pressure to the subject's medial hamstring muscles when worn by the subject without extending over any other part of the leg or knee covered by the flexible sleeve; and
- a second hamstring buttress configured to cover and apply pressure to the subject's semimembranosus and semitendinosus muscles when worn by the subject without extending over other parts of the leg or knee covered by the flexible sleeve.

\* \* \* \* \*